US00PP23152P2

(12) United States Plant Patent
Pieters

(10) Patent No.: US PP23,152 P2
(45) Date of Patent: Oct. 30, 2012

(54) ***CHRYSANTHEMUM* PLANT NAMED 'FIRE SPRINTER'**

(50) Latin Name: *Chrysanthemum×morifolium*
Varietal Denomination: Fire Sprinter

(75) Inventor: Luc Remi Johan Pieters, Staden-Oostnieuwkerke (BE)

(73) Assignee: Pieters Joseph & Luc B.V.B.A., Staden-Oostnieuwkerke (BE)

( * ) Notice: Subject to any disclaimer, the term of this patent is extended or adjusted under 35 U.S.C. 154(b) by 0 days.

(21) Appl. No.: 13/066,459

(22) Filed: Apr. 14, 2011

(51) Int. Cl.
*A01H 5/00* (2006.01)

(52) U.S. Cl. ..... Plt./298

(58) Field of Classification Search ..... Plt./298
See application file for complete search history.

*Primary Examiner* — Annette Para
(74) *Attorney, Agent, or Firm* — C. A. Whealy

(57) ABSTRACT

A new and distinct cultivar of *Chrysanthemum* plant named 'Fire Sprinter', characterized by its uniform, upright, outwardly spreading and rounded plant habit; moderately vigorous growth habit; freely branching habit; dense and full plant habit; uniform and freely flowering habit; decorative-type inflorescences with bright greyed red-colored ray florets; long flowering period; and excellent garden performance.

2 Drawing Sheets

Botanical designation: *Chrysanthemum×morifolium.*
Cultivar denomination: 'FIRE SPRINTER'.

BACKGROUND OF THE INVENTION

The present invention relates to a new and distinct cultivar of *Chrysanthemum* plant, botanically known as *Chrysanthemum×morifolium* and hereinafter referred to by the name 'Fire Sprinter'.

The new *Chrysanthemum* plant is a product of a planned breeding program conducted by the Inventor in Staden-Oostnieuwkerke, Belgium. The objective of the breeding program is to create new freely flowering *Chrysanthemum* plants with unique and attractive ray floret coloration.

The new *Chrysanthemum* plant originated from a cross-pollination made by the Inventor in Staden-Oostnieuwkerke, Belgium in October, 2006 of *Chrysanthemum×morifolium* 'Early Surfer', not patented, as the female, or seed, parent with *Chrysanthemum×morifolium* 'Padre', not patented. The new *Chrysanthemum* plant was discovered and selected by the Inventor as a flowering plant from within the progeny of the stated cross-pollination in a controlled greenhouse environment in Staden-Oostnieuwkerke, Belgium in October, 2007.

Asexual reproduction of the new *Chrysanthemum* plant by vegetative cuttings was first conducted in a controlled greenhouse environment in Staden-Oostnieuwkerke, Belgium in February, 2008. Asexual reproduction by cuttings has shown that the unique features of this new *Chrysanthemum* plant are stable and reproduced true to type in successive generations.

SUMMARY OF THE INVENTION

Plants of the new *Chrysanthemum* have not been observed under all possible environmental conditions and cultural conditions. The phenotype may vary somewhat with variations in environment such as temperature, daylength and light intensity, without, however, any variance in genotype.

The following traits have been repeatedly observed and are determined to be the unique characteristics of 'Fire Sprinter'.

These characteristics in combination distinguish 'Fire Sprinter' as a new and distinct *Chrysanthemum* plant:

1. Uniform, upright, outwardly spreading and rounded plant habit; moderately vigorous growth habit.
2. Freely branching habit; dense and full plant habit.
3. Uniform and freely flowering habit.
4. Decorative-type inflorescences with bright greyed red-colored ray florets.
5. Long flowering period.
6. Excellent garden performance.

Plants of the new *Chrysanthemum* differ primarily from the female parent, 'Early Surfer', in the following characteristics:

1. Grown under natural season conditions, plants of the new *Chrysanthemum* flower about five days earlier than plants of 'Early Surfer'.
2. Plants of the new *Chrysanthemum* and 'Early Surfer' differ in ray floret color as plants of 'Early Surfer' have pink-colored ray florets.

Plants of the new *Chrysanthemum* differ primarily from the male parent, 'Padre', in the following characteristics:

1. Grown under natural season conditions, plants of the new *Chrysanthemum* flower about five days earlier than plants of 'Padre'.
2. Plants of the new *Chrysanthemum* flower more uniformly than plants of 'Padre'.
3. Plants of the new *Chrysanthemum* and 'Padre' differ in ray floret color as plants of 'Early Surfer' have pink-colored ray florets.

Plants of the new *Chrysanthemum* can also be compared to plants of *Chrysanthemum×morifolium* 'Fuschini Red', not patented. In side-by-side comparisons conducted in Staden-Oostnieuwkerke, Belgium, plants of the new *Chrysanthemum* differed from plants of 'Fuschini Red' in the following characteristics:

1. Plants of the new *Chrysanthemum* had decorative type inflorescences whereas plants of 'Fuschini Red' had pompon type inflorescences.
2. Plants of the new *Chrysanthemum* had larger inflorescences than plants of 'Fuschini Red'.

BRIEF DESCRIPTION OF THE PHOTOGRAPHS

The accompanying photographs illustrate the overall appearance of the new *Chrysanthemum* plant showing the colors as true as it is reasonably possible to obtain in colored reproductions of this type. Colors in the photographs may differ slightly from the color values cited in the detailed botanical description which accurately describe the colors of the new *Chrysanthemum* plant.

The photograph on the first sheet comprises a side perspective view of a typical flowering plant of 'Fire Sprinter' grown in a container.

The photograph on the second sheet are close-up views of the upper and lower surfaces of typical inflorescences (left) of 'Fire Sprinter' and upper and lower surfaces of typical leaves (right) of 'Fire Sprinter'.

DETAILED BOTANICAL DESCRIPTION

The aforementioned photographs and following observations and measurements describe plants grown during the summer and autumn in 19-cm containers in an outdoor nursery in Staden-Oostnieuwkerke, Belgium and under conditions and practices which approximate those generally used in commercial *Chrysanthemum* production. During the production of the plants, day temperatures ranged from 10° C. to 25° C. and night temperatures ranged from 5° C. to 15° C. Plants were 5.5 months old when the photographs and description were taken. In the following description, color references are made to The Royal Horticultural Society Colour Chart, 2007 Edition, except where general terms of ordinary dictionary significance are used.

Botanical classification: *Chrysanthemum×morifolium* 'Fire Sprinter'.

Parentage:

*Female, or seed, parent.*—*Chrysanthemum×morifolium* 'Early Surfer', not patented.

*Male, or pollen, parent.*—*Chrysanthemum×morifolium* 'Padre', not patented.

Propagation:

*Type*.—Terminal vegetative cuttings.

*Time to initiate roots, summer*.—About 14 days at temperatures of about 20° C.

*Time to initiate roots, winter*.—About 20 days at temperatures of about 20° C.

*Time to produce a rooted young plant, summer*.—About 30 days at temperatures of about 20° C.

*Time to produce a rooted young plant, winter*.—About 40 days at temperatures of about 20° C.

*Root description*.—Fine, fibrous; light brown in color.

*Rooting habit*.—Freely branching; medium density.

Plant description:

*Appearance*.—Perennial *Chrysanthemum* with decorative type inflorescences; stems upright and outwardly spreading giving a uniformly rounded appearance to the plant; very freely branching habit with about 80 lateral branches developing per plant; pinching enhances lateral branch development; dense and full plant habit; moderately vigorous growth habit.

*Plant height*.—About 41.3 cm.

*Plant width*.—About 68.5 cm.

*Lateral branches*.—Length: About 20.3 cm. Diameter: About 4 mm. Internode length: About 2.7 cm. Strength: Strong. Aspect: Lateral branches positioned about 40° from the main stem. Texture: Densely pubescent; longitudinally ridged. Color: Close to 143A to 143B.

*Leaves*.—Arrangement: Alternate, simple. Length: About 3.1 cm. Width: About 2.8 cm. Shape: Roughly ovate, three to five-lobed. Apex: Acute. Base: Attenuate. Margin: Palmately lobed and coarsely dentate, sinuses between lateral lobes divergent to parallel. Texture, upper surface: Slightly pubescent. Texture, lower surface: Densely pubescent. Venation pattern: Pinnate. Color: Developing leaves, upper surface: Close to 137B. Developing leaves, lower surface: Close to 138B. Fully expanded leaves, upper surface: Close to 137B; venation, close to 137B to 137C. Fully expanded leaves, lower surface: Close to 147B; venation, close to 147B to 147C. Petiole: Length: About 9 mm. Diameter: About 1.5 mm. Texture, upper and lower surfaces: Densely pubescent. Color, upper surface: Close to 138B. Color, lower surface: Close to 138A to 138B.

Inflorescence description:

*Appearance*.—Decorative inflorescence form; inflorescences borne on terminals above foliar plane; disc and ray florets arranged acropetally on a capitulum.

*Fragrance*.—Moderately fragrant, pungent.

*Flowering response*.—Long flowering period; under natural season conditions, plants flower continuously from mid-September to late October in Belgium.

*Postproduction longevity*.—Inflorescences maintain good color and substance for about three weeks in an outdoor nursery; inflorescences not persistent.

*Quantity of inflorescences*.—About 23 inflorescences develop per lateral branch; about 1,500 inflorescences per plant.

*Inflorescence bud*.—Height: About 8 mm. Diameter: About 7 mm. Shape: Broadly ovate. Color: Close to 138A to 138B.

*Inflorescence size*.—Diameter: About 3.6 cm. Depth (height): About 2 cm. Disc diameter: About 7 mm. Receptacle diameter: About 3 mm. Receptacle height: About 3 mm. Receptacle color: Close to 145B.

*Ray florets*.—Length: About 1.8 cm. Width: About 4 mm. Shape: Narrowly oblong to oblanceolate. Apex: Obtuse to broadly acute. Base: Cuneate. Margin: Entire. Aspect: About 70° from vertical. Texture, upper and lower surfaces: Smooth, glabrous; longitudinally ridged. Number of ray florets per inflorescence: About 100. Color: When opening, upper surface: Close to 180A; at the base, close to 150A. When opening, lower surface: Close to 177C to 177D; at the base, close to 144C. Fully opened, upper surface: Close to 180A to 180D; towards the base, close to 180C; at the base, close to 150A; color becoming closer to 183B with development. Fully opened, lower surface: Close to 165D; at the base, close to 144C to 144D; color becoming closer to 178B with development.

*Disc florets*.—Length: About 8 mm. Diameter: About 1 mm. Shape: Tubular, filiform; apices narrowly acute. Texture, inner and outer surfaces: Smooth, glabrous. Number of disc florets per inflorescence: About 50 massed at the center of the inflorescence. Color, immature: Close to 183B; at the base, close to 150B to 150C. Color, mature: Close to 183B; at the base, close to 150B to 150C.

*Phyllaries*.—Number of phyllaries per inflorescence: About 24 arranged in about three whorls. Length: About 6 mm. Width: About 2.5 mm. Shape: Ovate. Apex: Bluntly acute. Base: Cuneate. Margin: Entire. Texture, upper surface: Smooth, glabrous. Texture, lower surface: Pubescent. Color, upper surface: Close to 143B; margins, close to N199A. Color, lower surface: Close to 138A to 138B; margins, close to N199A.

*Peduncles*.—Length, terminal peduncle: About 6.4 cm. Length, fourth peduncle: About 5.2 cm. Diameter: About 1.5 mm. Aspect: Erect to about 30° from vertical. Strength: Strong. Texture: Densely pubescent. Color: Close to 138B.

*Reproductive organs*.—Androecium: Not observed. Gynoecium: Present only on ray florets. Quantity: One pistil per floret. Pistil length: About 5 mm. Style length: About 4 mm. Style color: Close to 154B. Stigma shape: Cleft, decurrent. Stigma color: Close to 4A. Ovary color: Close to 144C to 144D.

*Seed/fruit*.—Seed and fruit production have not been observed.

Disease/pest resistance: Resistance to pathogens and pests common to *Chrysanthemums* has not been observed on plants grown under commercial conditions.

Garden performance: Plants of the new *Chrysanthemum* have demonstrated excellent garden performance, are hardy to USDA Hardiness Zones 7 to 8 and will tolerate high temperatures of about 35° C.

It is claimed:

1. A new and distinct *Chrysanthemum* plant named 'Fire Sprinter' as illustrated and described.

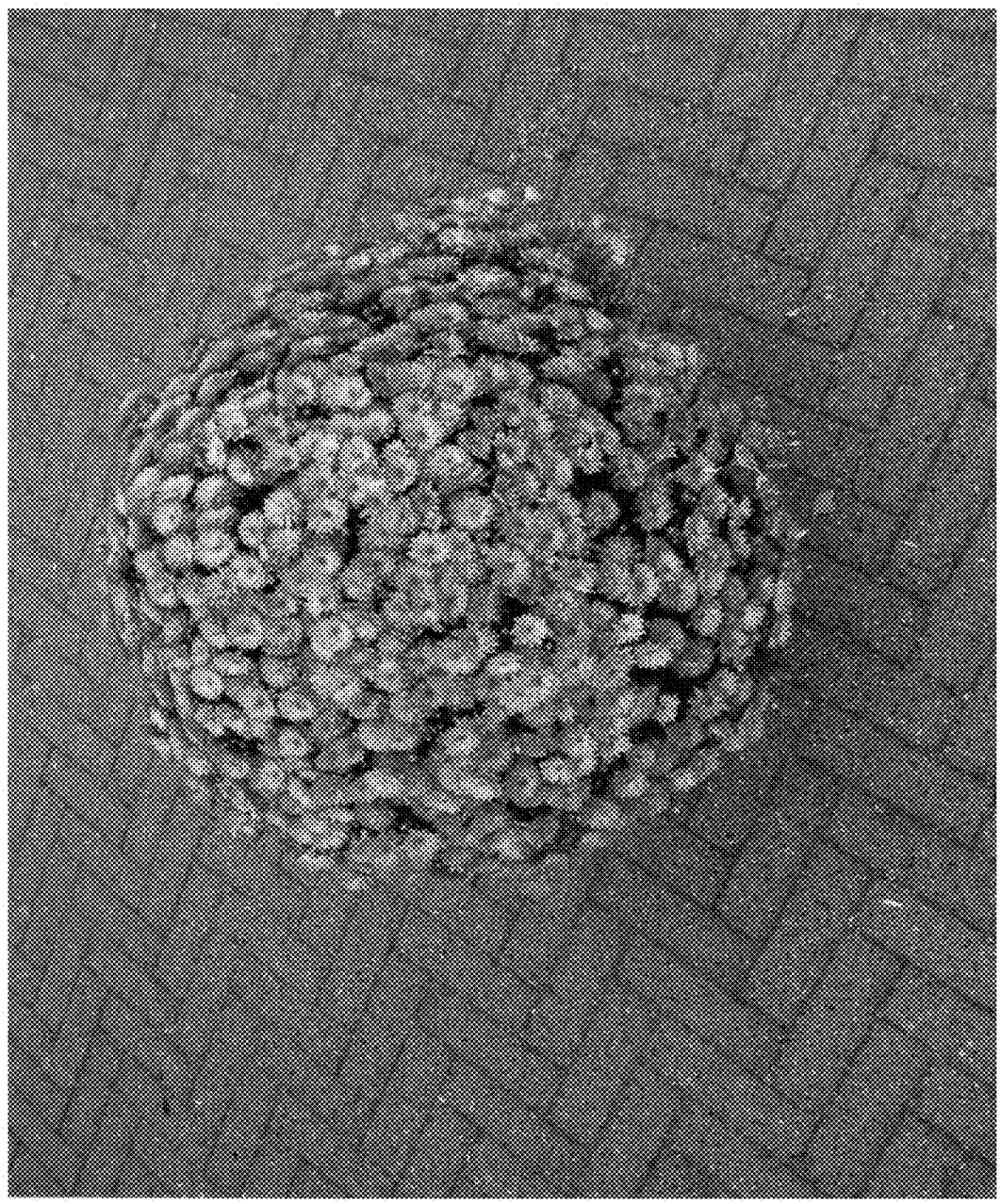

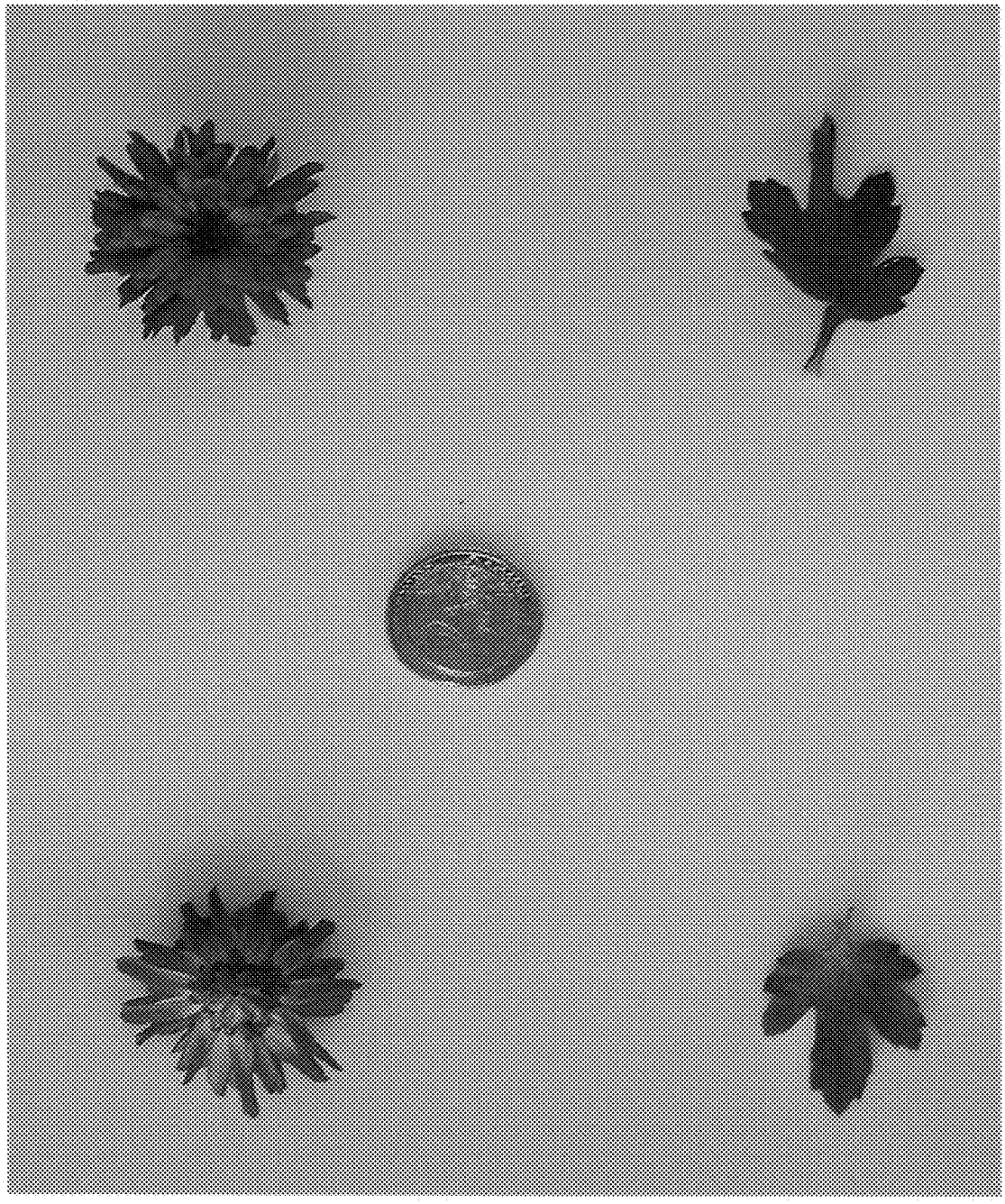

* * * * *